(12) United States Patent
Chappo

(10) Patent No.: US 10,877,168 B2
(45) Date of Patent: Dec. 29, 2020

(54) NANO-MATERIAL IMAGING DETECTOR WITH AN INTEGRAL PIXEL BORDER

(71) Applicant: KONINKLIJKE PHILIPS N.V., Eindhoven (NL)

(72) Inventor: Marc Anthony Chappo, Elyria, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/076,731

(22) PCT Filed: Mar. 15, 2017

(86) PCT No.: PCT/IB2017/051481
§ 371 (c)(1),
(2) Date: Aug. 9, 2018

(87) PCT Pub. No.: WO2017/163149
PCT Pub. Date: Sep. 28, 2017

(65) Prior Publication Data
US 2019/0049601 A1  Feb. 14, 2019

Related U.S. Application Data

(60) Provisional application No. 62/312,083, filed on Mar. 23, 2016.

(51) Int. Cl.
*G01T 1/24* (2006.01)
*G01T 1/29* (2006.01)
(Continued)

(52) U.S. Cl.
CPC .............. *G01T 1/24* (2013.01); *A61B 6/4233* (2013.01); *G01T 1/16* (2013.01); *G01T 1/2928* (2013.01)

(58) Field of Classification Search
CPC ........ G01T 1/24; G01T 1/2928; A61B 6/4233
(Continued)

(56) References Cited

U.S. PATENT DOCUMENTS 5,710,436 A * 1/1998 Tanamoto .............. B82Y 10/00
257/14
7,126,136 B2  10/2006 Chen
(Continued)

FOREIGN PATENT DOCUMENTS

DE      102011083532       2/2013
WO        2014147570       9/2014

OTHER PUBLICATIONS

Urdaneta, et al: "Porous silicon-based quantum dot broad spectrum radiation detector", Journal of Instrumentation, Institute of Physics Publishing, Bristol, GB, vol. 6, No. 1, Jan. 11, 2011.

*Primary Examiner* — Taeho Jo
(74) *Attorney, Agent, or Firm* — Larry Liberchuk

(57) ABSTRACT

A radiation detector array (112) of an imaging system (100) comprises a plurality of detector modules (114). Each of the plurality of detector modules includes a plurality of detector pixel (116). Each of the plurality of detector pixels includes an integral pixel border (202, 204, 206, 208) and a direct conversion active area within the integral pixel border. A method comprises receiving radiation with a nano-material detector pixel that includes an integral pixel border, generating, with the detector pixel, a signal indicative of an energy of the received radiation, while reducing pixel signal crosstalk, and reconstructing the signal to construct an image. An imaging system (100) comprises a source of X-ray radiation configured to emit X-ray radiation that traverses an examination region, a nano-material imaging detector with an integral pixel border, wherein the nano-material imaging detector is configured to detect X-ray radiation, and a
(Continued)

reconstructor configured to reconstruct an output of the nano-material imaging detector to produce a CT image.

17 Claims, 2 Drawing Sheets

(51) Int. Cl.
    *A61B 6/00*          (2006.01)
    *G01T 1/16*          (2006.01)

(58) Field of Classification Search
    USPC .......................................................... 378/19
    See application file for complete search history.

(56) References Cited

U.S. PATENT DOCUMENTS

| | | | |
|---|---|---|---|
| 7,773,404 B2 | 8/2010 | Sargent | |
| 7,972,885 B1* | 7/2011 | Dutta | H01L 31/0352 438/48 |
| 7,977,643 B2 | 7/2011 | Weinberg | |
| 8,017,906 B2* | 9/2011 | Nelson | G01T 1/2018 250/252.1 |
| 8,035,184 B1* | 10/2011 | Dutta | B82Y 20/00 257/443 |
| 9,222,907 B2* | 12/2015 | Prasad | G01N 27/3278 |
| 2002/0172820 A1* | 11/2002 | Majumdar | B82Y 20/00 428/357 |
| 2005/0161662 A1* | 7/2005 | Majumdar | H01L 33/24 257/18 |
| 2007/0003006 A1* | 1/2007 | Tkaczyk | G01T 1/243 378/19 |
| 2007/0164270 A1* | 7/2007 | Majumdar | G02B 6/107 257/14 |
| 2009/0179155 A1* | 7/2009 | Weinberg | G01T 1/24 250/370.01 |
| 2009/0217967 A1* | 9/2009 | Hovel | H01L 31/0304 136/249 |
| 2010/0002324 A1* | 1/2010 | Rozhin | C08J 5/005 359/896 |
| 2010/0003516 A1* | 1/2010 | Majumdar | G02B 6/107 428/368 |
| 2010/0270462 A1* | 10/2010 | Nelson | G01T 1/202 250/252.1 |
| 2010/0289001 A1* | 11/2010 | Kahen | C09K 11/883 257/13 |
| 2011/0024685 A1* | 2/2011 | Clothier | C01F 17/253 252/301.45 |
| 2012/0121067 A1* | 5/2012 | Hayden | G01T 1/2018 378/62 |
| 2012/0199747 A1 | 8/2012 | Letant | |
| 2013/0028379 A1* | 1/2013 | Nelson | H01L 27/14601 378/62 |
| 2013/0099342 A1* | 4/2013 | Fonash | H01L 31/03529 257/432 |
| 2013/0187053 A1* | 7/2013 | Colby | B82Y 15/00 250/366 |
| 2013/0270517 A1* | 10/2013 | Nozawa | H01L 33/04 257/13 |
| 2014/0051975 A1* | 2/2014 | Rapoport | A61B 6/508 600/411 |
| 2015/0221697 A1* | 8/2015 | Colby | B82Y 15/00 378/98.8 |
| 2016/0245932 A1* | 8/2016 | Blevis | A61B 6/037 |
| 2018/0203134 A1 | 7/2018 | Chappo | |

\* cited by examiner

NANO-MATERIAL IMAGING DETECTOR WITH AN INTEGRAL PIXEL BORDER

CROSS REFERENCE TO RELATED APPLICATIONS

This application is the U.S. National Phase application under 35 U.S.C. § 371 of International Application No. PCT/IB2017/051481, filed Mar. 15, 2017, published as WO 2017/163149 on Sep. 28, 2017, which claims the benefit of U.S. Provisional Patent Application No. 62/312,083 filed Mar. 23, 2016. These applications are hereby incorporated by reference herein.

FIELD OF THE INVENTION

The following generally relates to an imaging detector and more particularly to a nano-material imaging detector with an integral pixel border, and is described with particular application to computed tomography (CT); however, the following is also amenable to other imaging modalities such as X-ray, positron emission tomography (PET), CT/PET, CT/MR (magnetic resonance), PET/MR, and/or other imaging system configured to detect radiation in one or more energy bands and directly convert the detected radiation to an electrical signal indicative thereof, including diagnostic, security, non-destructive, etc. imaging systems.

BACKGROUND OF THE INVENTION

Direct converter spectral (multi-energy) CT detectors include a direct conversion material such as Cadmium Telluride (CdTe), Cadmium Zinc Telluride (CZT), Silicon (Si), etc. The direct conversion material directly converts X-ray photons incident thereon into electrical currents or pulses. This is in contrast to indirect converter CT detectors such a scintillator/photodiode based detectors where the scintillator converts such X-ray photons to light photons, and the photodiode converts the light photons to the electrical currents or pulses.

Technologies, such as Quantum Dots (QDs) in conjunction with porous Silicon (pSi), are being applied to direct converter detectors. The goal is a lower cost spectral CT detector with improved radiation stopping power and the ability to tailor the response such that improved detection efficiency (DE) and resolution can simultaneously be realized. However, such detectors are susceptible to cross-talk, which, generally, is when a signal generated in one or more pixels crosses over into another pixel, which can lead to signal measurement error for all pixels involved.

Unfortunately, such cross-talk can lead to visible artifacts and/or reduced spatial resolution in the reconstructed CT image. Software and/or hardware corrections for cross-talk are contemplated to address these shortcomings in performance. However, high pulse rates cause errors in the corrections, and the hardware-based corrections are susceptible to threshold differences between pixels, which yields improper summing of charge. In view of at least the above, there is an unresolved need for another detector configuration.

SUMMARY OF THE INVENTION

Aspects of the present application address the above-referenced matters and others.

According to one aspect, a radiation detector array of an imaging system comprises a plurality of detector modules. Each of the plurality of detector modules includes a plurality of detector pixels. Each of the plurality of detector pixels includes an integral pixel border and a direct conversion active area within the integral pixel border.

In another aspect, a method comprises receiving radiation with a nano-material detector pixel that includes an integral pixel border. The method further comprises generating, with the detector pixel, a signal indicative of an energy of the received radiation. The method further comprises reconstructing the signal to construct an image.

In another aspect, an imaging system comprises a source of X-ray radiation configured to emit X-ray radiation that traverses an examination region. The imaging system further comprises a nano-material imaging detector with an integral pixel border. The nano-material imaging detector is configured to detect X-ray radiation. The imaging system further comprises a reconstructor configured to reconstruct an output of the nano-material imaging detector to produce a CT image.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
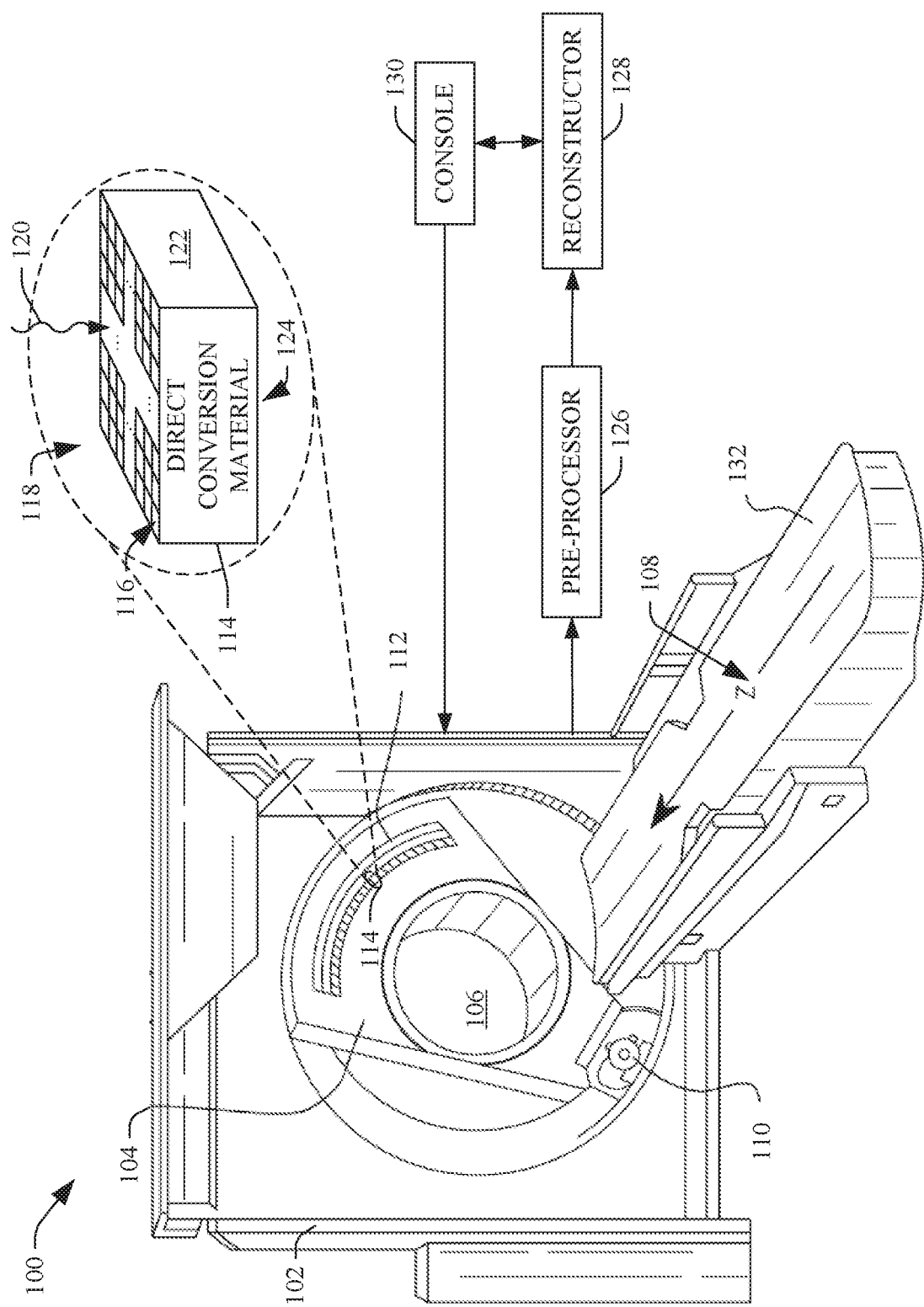
FIG. 1 schematically illustrates an example imaging system with a nano-material imaging detector having an integral pixel border.

FIG. 1 schematically illustrates an example imaging system 100 such as a computed tomography (CT) system.

The imaging system 100 includes a stationary gantry 102 and a rotating gantry 104, which is rotatably supported by the stationary gantry 102. The rotating gantry 104 rotates around an examination region 106 about a longitudinal or z-axis 108. A radiation source 110, such as an x-ray tube, is supported by the rotating gantry 104, rotates therewith, and generates and emits poly-energetic/chromatic radiation.

A radiation sensitive detector array 112 includes one or more rows of detector modules 114 arranged with respect to each other along the z-axis 108 direction. Each module 114 includes an array of detector pixels 116 and a radiation receiving surface 118. Each detector pixel 116 is configured to detect X-ray photons 120 traversing the examination region 106 and impinging on the radiation receiving surface 118. Each detector pixel 116 includes a direct conversion material 122 configured to directly convert X-ray radiation to an electrical signal or pulse, or a pulse with a peak amplitude indicative of an energy thereof.

As described in greater detail below, the direct conversion material 122 includes a first material with a plurality of columns extending from the radiation receiving surface 118 towards an opposing side 124, which opposes the radiation receiving surface 118, a second different (nano-) material disposed in inner columns of the pixel 116, and a third (nano-)material, which is different from the first and the second materials, disposed in columns of the pixel 116 surrounding the inner columns, wherein the first and second materials interact to produce electron-hole pairs, and the third material provides an integral pixel border or boundary for a pixel 116. The interaction of the first and second materials directly convert received X-ray radiation to an electrical signal or pulse (via electron-hole pair generation), which can be read out from the direct conversion material 122 with suitable electronics, e.g., contained in an Application Specific Integrated Circuit (ASIC). The third material (i.e., the pixel border) reduces electrical cross-talk between pixels 116. This configuration of materials can also improve geometric efficiency relative to other types of indirect and direct conversion detectors.

A pre-processor 126 includes an energy discriminator configured to energy-discriminate the signals or pulses from each detector pixel 116 through, e.g., one or more comparators, each having a different energy threshold, which correspond to an energy of interest. The pre-processor 126 further includes a counter that increments a count value for each threshold based on the output of the energy discriminator. The pre-processor 126 further includes a binner that energy-bins the signals and, hence, the detected radiation, into two or more energy bins based on the counts, wherein an energy bin encompasses an energy window.

A reconstructor 128 is configured to selectively reconstruct the detected signals. In one instance, the reconstructor 128 reconstructs signals for a particular energy range. For instance, the reconstructor 128 can reconstructs signals one or more energies or energy ranges in the diagnostic range of 20 keV to 140 keV. In another instance, the reconstructor 128 combines signals for all of the bins and reconstructs the combined signal to generate a conventional image over the energy spectrum of the emitted radiation.

An operator console 130 includes a human readable output device such as a monitor or display and an input device such as a keyboard and mouse. Software resident on the console 130 allows the operator to interact with the system 100 via a graphical user interface (GUI) or otherwise. This interaction may include selecting a type of scan, selecting an imaging protocol, initiating scanning, etc.

A subject support 132 such as a couch supports a human or animal patient or an object in the examination region 106. The subject support 132 is movable in coordination with scanning so as to guide the subject or object with respect to the examination region 106 for performing a scan of the subject or object.

In other embodiments, the imaging system 100 includes X-ray, PET, CT/PET, CT/MR, PET/MR, etc. imaging system. It is to be appreciated that suitable materials are utilized to convert radiation photons of desired energy(s) to signals or pulses depending on the particular imaging system.

Figure 2:
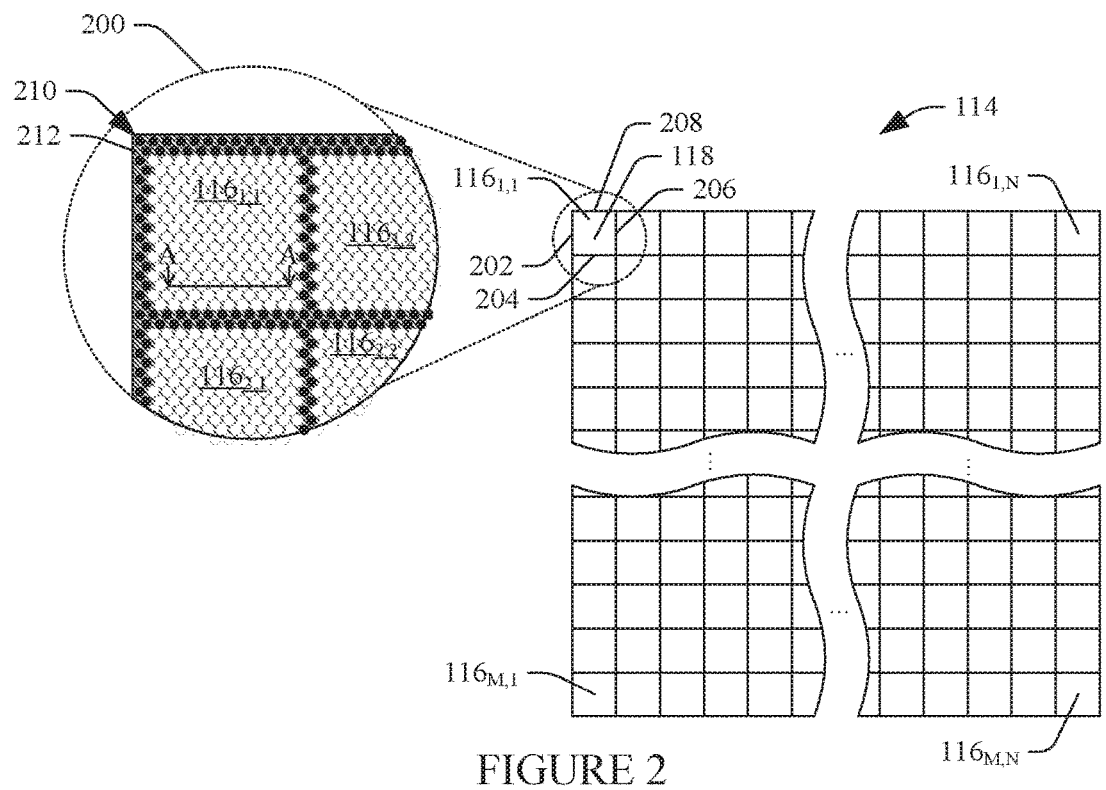
FIG. 2 schematically illustrates a top down view of a detector module of the nano-material imaging detector with the integral pixel border.
Figure 3:
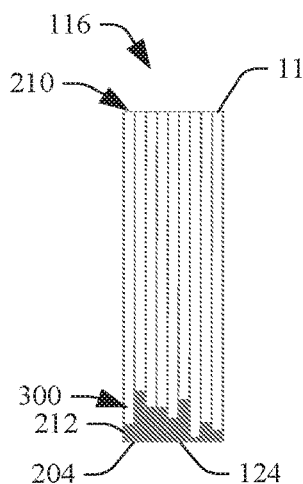
FIG. 3 schematically illustrates a cross-sectional view a detector pixel of the detector module of the nano-material imaging detector with the integral pixel border.

FIGS. 2 and 3 together schematically illustrate an example of a sub-portion of the detector module 114. FIG. 2 schematically illustrates a top down view looking into the radiation receiving surface 118 of the detector module 114, and FIG. 3 schematically illustrates a cross-sectional view of a single detector pixel 116 of FIG. 2 along line A-A of FIG. 2.

In FIG. 2, the detector module 114 includes a two-dimensional (2-D) matrix of detector pixels 116, including pixels $116_{1,1}, \ldots, 116_{1,N}, \ldots, 116_{M,1}, \ldots, 116_{M,N}$. The detector pixel $116_{1,1}$ includes sides 202, 204, 206, and 208.

FIG. 3 shows a view from one of the sides 202, 204, 206, or 208, and also shows the radiation receiving surface 118 and the opposing side 124.

The pixel $116_{1,1}$ comprises a plurality of columns 210 in a first material 212. In the magnified view at 200, each column 210 is represented as a circle. A "white" columns represents a column 210 filled with the second material. A "black" column represents a column filled with the third material. The first material is shown as "gray." The circle shape is not limiting. Other shapes such as elliptical, square, rectangular, octagonal, irregular, etc. are contemplated herein.

The combination of the "white" columns and the first material 212 within the "black" columns provide the direct conversion material 122, as discussed herein, via interaction there between resulting in electron-hole pairs. The "black" columns provide an integral pixel border (or the sides 202-28) for the pixel $116_{1,1}$. This border is integral in that the border is part of and in the pixel $116_{1,1}$ itself; namely, certain columns 210 of the direct conversion material 122 filled with the third material.

FIG. 3 shows, at 300, the "white" columns 210 along A-A are not all the same length. For example, the columns 210 begin at the radiation receiving surface 118. However, different columns 210 end at different depths in first ("gray") material 212, with the third and fourth columns 210 ending at the same depth. In other embodiments, all columns have the same length, no columns have the same length, and/or more than two columns have the same length. The length variation corresponds to the pSi fabrication techniques used to create the columns.

A specific but non-limiting example is provided next.

In this example, the first material includes porous silicon (pSi), the second material includes lead sulphide (PbS), and the third material includes lead (Pb) (or Titanium (Ti), or other material). Columns diameters can be on the order of tens of nanometers (nm) and depths on the order of 300 micrometers (μm). For PbS, a depth of approximately 300 microns produces sufficient stopping power for efficient direct conversion of CT X-ray photons. It is to be understood that these materials and/or dimensions are only examples and can be changed to provide desired results for various imaging applications. Such results include using conductive pixel borders segmented to allow collecting charge on one side, as well as encapsulated insulative materials which can make pixel boundaries that are not part of the charge collection process. It is also contemplated that these pixels may be small enough to be considered sub-pixels of a larger pixel depending on the X-Ray flux required for the application.

Standard pSi fabrication techniques such as Anodic and/or other etching of Si can produce the columns 210 of sufficient diameter for the QDs and depth for the required radiation stopping power that leads to conversion efficiency. The second material includes microscopic (nano-material) encapsulated PbS in the form of quantum dots (QDs) or the like that fit into the columns to fill them to the desired depth. The third material includes microscopic (nano-material) encapsulated Pb in the form of quantum dots (QDs) or the like that likewise fit into the columns to fill them to the desired depth.

Insertion of the PbS QDs and/or the Pb QDs can be through masks. For example, a first mask can be used to mask certain columns so that other columns can be filled with the PbS QDs (or Pb QDs). Then, a second mask can be used to mask the filled columns so that the remaining unfilled columns can be filled with the Pb QDs (or PbS QDs). Any excess PbS QDs and/or Pb QDs can be removed. Other approaches are also contemplated herein.

The columns of PbS QDs make up the majority of the columns 210 of the pixel 116 and represent the active area. The columns of Pb QDs make up the integral border of the pixel 116. This border may be comprised of multiple columns (as shown in FIG. 2) as part of a trade-off in the design of crosstalk versus geometric efficiency and consideration for detector resolution. This particular non-limiting choice of pixel border material can also minimize X-Ray scatter within a pixel from escaping to neighboring pixels, thus eliminating another potential cause of crosstalk. The border columns can be insulated from the Si with oxide or other suitable material and electrically connected at one or more points via a metallization. The fabrication used for pSi QDs can be also utilized for the pixel borders.

An example of an encapsulate material with quantum dots of scintillation material embedded therein is described in EP 14186022.1, filed Sep. 23, 2014, and entitled "Encapsulated materials in porous particles," the entirety of which is incorporated herein by reference. An example of a quantum dot detector is described in application Ser. No. 62/202,397, filed Aug. 7, 2015, and entitled "QUANTUM DOT BASED IMAGING DETECTOR," the entirety of which is incorporated herein by reference.

Figure 4:
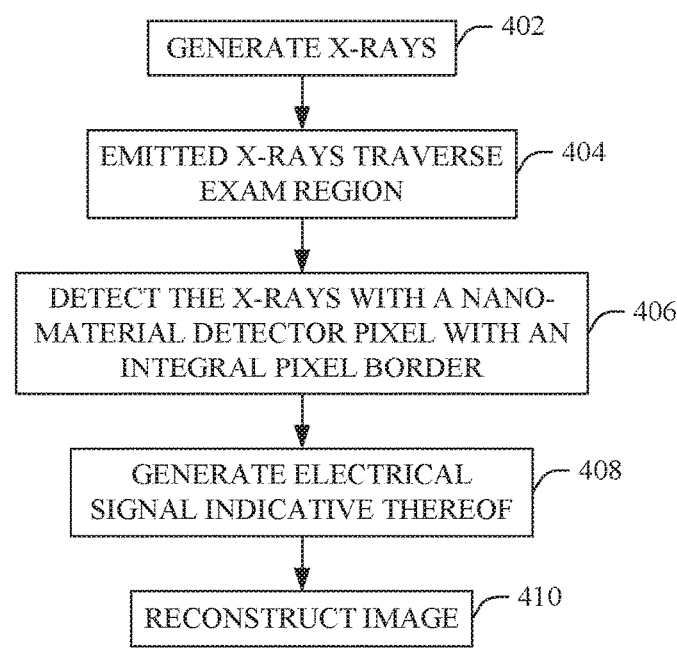
FIG. 4 illustrates an example method in accordance with an embodiment herein.

FIG. 4 illustrates imaging with the detector array 112.

It is to be appreciated that the ordering of the below acts is for explanatory purposes and not limiting. As such, other orderings are also contemplated herein. In addition, one or more of the acts may be omitted and/or one or more other acts may be included.

At 402, X-ray radiation is generated by an X-ray tube.

At 404, the X-ray radiation is emitted and traverses an examination field.

At 406, the detector array 112 detects the transmission radiation traversing the examination field of view. As described herein, the detector array 112 includes the detector modules 114 with the nano-material detector pixels 116 with an integral pixel border.

At 408, an electrical signal or pulse indicative of an energy of the detected X-ray radiation is generated.

At 410, the electrical signal or pulse is processed to generate a spectral or non-spectral image of the examination field of view, including a portion of the patient therein.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method for detecting radiation in an imaging system, comprising:
   receiving radiation with a nanomaterial detector pixel that includes an integral pixel border and a first set of columns located within a first material;
   attenuating radiation that traverses a first nanomaterial disposed in the first set of columns;
   generating, with the nanomaterial detector pixel, a signal indicative of an energy of the received radiation; and
   reconstructing the signal to construct an image.

2. The method according to claim 1, wherein the nanomaterial detector pixel includes a second set of columns located within the first material and surrounded by the first set of columns, and further comprising: converting the received radiation traversing the second set of columns to an electrical signal or pulse through an interaction of a second nanomaterial disposed in the second set of columns and the first material.

3. The method according to claim 2, further comprising:
   generating a first signal indicative of a first energy of a first photon with one of the columns of the second set of columns; and
   generating a second signal indicative of a second energy of a second photon with another one of the columns of the second set of columns, wherein the first and second energies are different energies.

4. A radiation detector array of an imaging system, comprising:
   a plurality of detector modules, each detector module including a plurality of nanomaterial detector pixels, each nanomaterial detector pixel receiving radiation and being configured to include an integral pixel border and a first set of columns located within a first material such that the received radiation is attenuated when traversing a first nanomaterial disposed in the first set of columns, wherein each nanomaterial detector pixel generates a signal indicative of an energy of the received radiation; and
   at least one processor configured to reconstruct the signal and construct an image based on the reconstructed signal.

5. The radiation detection system according to claim 4, wherein the first nanomaterial includes a plurality of quantum dots.

6. The radiation detection system according to claim 4, wherein the first nanomaterial includes at least one of lead and titanium.

7. The radiation detection system according to claim 4, wherein each nanomaterial detector pixel further includes a second nanomaterial disposed in a second plurality of columns.

8. The radiation detection system according to claim 7, wherein the second nanomaterial is a direct conversion active area within the integral pixel border.

9. The radiation detection system according to claim 7, wherein the second nanomaterial includes a plurality of quantum dots.

10. The radiation detection system according to claim 7, wherein the second nanomaterial includes lead sulphide.

11. The radiation detection system according to claim 7, wherein each column has a diameter on an order of tens of nanometers.

12. The radiation detection system according to claim 7, wherein each column has a length on an order of three hundred microns.

13. The radiation detection system according to claim 7, wherein the columns have a same length.

14. The radiation detection system according to claim 7, wherein at least two of the columns have a different length, and each different length corresponds to a different photon energy.

15. The radiation detection system according to claim 8, wherein the integral pixel border is electrically insulated from the direct conversion active area and electrically connected at one or more points via a metallization.

16. The radiation detection system according to claim 4, wherein at least one nanomaterial detector pixel includes sub-pixels that comprise the first set of columns located within the first material and the first nanomaterial disposed in the first set of columns.

17. A non-transitory computer-readable medium having one or more executable instructions stored thereon which, when executed by at least one processor, cause the at least one processor to perform a method for detecting radiation in an imaging system, the method comprising:
- receiving radiation with a nanomaterial detector pixel that includes an integral pixel border and a first set of columns located within a first material;
- attenuating radiation that traverses a first nanomaterial disposed in the first set of columns;
- generating, with the nanomaterial detector pixel, a signal indicative of an energy of the received radiation; and
- reconstructing the signal to construct an image.

* * * * *